United States Patent [19]

Honoré et al.

[11] Patent Number: 5,081,123
[45] Date of Patent: Jan. 14, 1992

[54] QUINOXALINE COMPOUND AND THEIR PREPARATION AND USE

[75] Inventors: Tage Honoré, K$\phi$penhagen; Poul Jacobsen, R$\phi$dovre; Flemming E. Nielsen, Virum; Lars Naerum, Gentofte, all of Denmark

[73] Assignee: Novo Nordisk A/S, Bagsvaerd, Denmark

[21] Appl. No.: 451,382

[22] Filed: Dec. 15, 1989

[30] Foreign Application Priority Data

Dec. 22, 1988 [DK] Denmark ............... 7161/88

[51] Int. Cl.$^5$ ............. C07D 241/38; C07D 471/04; C07D 217/02; A61K 31/495
[52] U.S. Cl. ............. 514/250; 544/344; 544/345; 546/143; 546/171; 560/22
[58] Field of Search ............. 544/344; 514/250

[56] References Cited

U.S. PATENT DOCUMENTS 4,977,155 12/1990 Jacobsen .............. 514/250

*Primary Examiner*—Mark L. Berch
*Attorney, Agent, or Firm*—Steve T. Zelson; Elias J. Lambiris

[57] ABSTRACT

Heterocyclic dihydroxyquinoxaline compounds having the formula

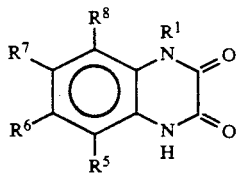

wherein $R^1$ is hydroxy, alkoxy, aryloxy, aralkyloxy, cycloalkylalkoxy, cycloalkoxy, or acyloxy;

$R^5$ and $R^6$ together form a further fused ring, which is substituted with hydrogen, halogen or CN, and $R^7$ and $R^8$ independently are hydrogen, $NO_2$, halogen, CN, $SO_2NR'R'$, $SO_2R'$, $CF_3$, or $OR'$, wherein $R'$ is hydrogen or $C_{1-4}$-alkyl; or $R^7$ and $R^8$ together form a further fused ring, which is substituted with hydrogen, halogen or CN, and $R^5$ and $r^6$ independently are hydrogen, $NO_2$, halogen, CN, $SO_2NR'R'$, $SO_2R'$, $CF_3$, or $OR'$, wherein $R'$ is hydrogen or $C_{1-4}$-alkyl.

The invention also relates to a method of preparing the compounds, pharmaceutical compositions thereof, and their use.

The compounds are useful in the treatment of indications caused by hyperactivity of the excitatory neurotransmitters, particularly the quisqualate receptors, and especially as neuroleptics.

9 Claims, No Drawings

QUINOXALINE COMPOUND AND THEIR PREPARATION AND USE

The present invention relates to therapeutically active heterocyclic compounds, a method of preparing the same, pharmaceutical compositions comprising the compounds, and a method of treating therewith.

L-glutamic acid, L-aspartic acid and a number of other closely related amino acids have in common the ability to activate neurons in the central nervous system (CNS). Biochemical, electrophysiological and pharmacological studies have substantiated this and demonstrated that acidic amino acids are transmitters for the vast majority of excitatory neurons in the mammalian CNS.

Interaction with glutamic acid mediated neurotransmission is considered a useful approach in the treatment of neurological and psychiatric diseases. Thus, known antagonists of excitatory amino acids have shown potent antiepileptic and muscle relaxant properties (A. Jones et al., Neurosci. Lett. 45, 157-61 (1984) and L. Turski et al., Neurosci. Lett. 53, 321-6 (1985)).

It has been suggested that accumulation of extracellular excitatory and neurotoxic amino acids, followed by hyperstimulation of neurons, may explain the neuronal degenerations seen in neurological diseases as Huntingtons chorea, Parkinsonism epilepsia senile dementia, and deficiencies of mental and motoric performance seen after conditions of brain ischemia, anoxia and hypoglycemia (E. G. McGeer et al., Nature, 263, 517-19 (1976) and R. Simon et al., Science, 226, 850-2 (1984).

Excitatory amino acids exert their actions via specific receptors located postsynaptically or presynaptically. Such receptors are at present conveniently subdivided into three groups based on electrophysiological and neurochemical evidence: 1 the NMDA (N-methyl-D-aspartate) receptors, 2 the quisqualate receptors, and 3 the kainate receptors. L-glutamic acid and L-aspartic acid probably activate all the above types of excitatory amino acid receptors and possibly other types as well.

The consequence of excitatory amino acid interaction with postsynaptic receptors is an increase in intracellular cGMP levels (G. A. Foster et al., Life Sci. 27, 215-21 (1980)) and an opening of $Na^+$-channels (A. Luini et al., Proc. Natl. Acad. Sci. 78, 3250-54 (1981)). $Na^+$-influx in the neurons will depolarize the neuronal membranes, initiate an action potential and ultimately lead to a release of transmitter substance from the nerve terminal. The effects of test compounds on the above mentioned secondary responses to receptor interaction can be tested in simple in vitro systems.

The above mentioned classification of excitatory amino acid receptors into NMDA, quisqualate, and kainate receptors is based primarily on the following electrophysiological and neurochemical findings.

1) N-methyl-D-aspartate (NMDA) receptors exhibit high selectivity for the excitant NMDA. Ibotenic acid, L-homocysteic acid, D-glutamic acid and trans-2,3-piperidine dicarboxylic acid (trans-2,3-PDA) exert a strong to moderate agonist activity on these receptors. The most potent and selective antagonists are the D-isomers of the 2-amino-5-phosphonocarboxylic acids, e.g., 2-amino-5-phosphono-valeric acid (D-APV) and 2-amino-7-phosphonoheptanoic acid (D-APH), while moderate antagonist activity is shown by the D-isomers of long chain 2-amino dicarboxylic acids (e.g.,D-2-amino-adipic acid) and long chain diaminodicarboxylic acids (e.g.,diaminopimelic acid). The NMDA-induced synaptical responses have been extensively investigated in the mammalian CNS, especially in the spinal cord (J. Davies et al., J. Physiol. 297, 621-35 (1979) and the responses have been shown to be strongly inhibited by $Mg^{2+}$.

2) Quisqualate receptors are activated selectively by quisqualic acid, other potent agonists being AMPA (2-amino-3-hydroxy-5-methyl-4-isoxazolepropionic acid) and L-glutamic acid. Glutamic acid diethyl ester GDEE) is a selective but very weak antagonist of this site. Quisqualate receptors are relatively insensitive to $Mg^{2+}$.

It is well known that an excitatory aminoacid projection from prefrontal cortex to nucleus accumbens ( a special part of the forebrain having dopamine neurons) exists (Christie et al.,J. Neurochem. 45, 477-82 (1985) ). Further it is well known that glutamate modulates the dopaminergic transmission in the striatum (Rudolph et al., Neurochem.int. 5, 479-86 (1983)) as well as the hyperactivity connected with presynaptic stimulation of the dopamine system with AMPA in nucleus accumbens (Arnt. Life Sci. 28. 1597-1603 (1981)).

Quisqualate antagonists are therefore useful as a new type of neuroleptic.

3) Kainate receptors. Excitatory responses to kainic acid are relatively insensitive to antagonism by NMDA-antagonists and by GDEE, and it has been proposed that kainic acid activates a third subclass of acidic amino acid receptor. Certain lactonized derivatives of kainic acid are selective antagonists (O. Goldberg et al., Neurosci. Lett. 23, 187-91 (1981)) and the dipeptide 3-glutamyl-glycine also shows some selectivity for kainate receptors. $Ca^{2+}$ but not $Mg^{2+}$ is a strong inhibitor of kainic acid binding.

The affinity of a substance for one or more of the different types of excitatory amino acid receptors may be studied in simple binding experiments. In essense, the method involves incubation of a particular selected radiolabelled ligand and the particular specific substance to be investigated with brain homogenate which contains the receptor. Measurement of receptor occupancy is made by determination of the radioactivity bound to the homogenate and subtraction of nonspecific binding.

Quisqualate receptor binding may be studied by using $^3H$-AM-PA as radioligand.

The influence of glutamic acid analogues on secondary effects of glutamate receptor interactions may be studied in vitro by using brain slices. Such experiments will provide information as to the efficacies (agonist/antagonist) of the test substances. This is in contrast to binding studies, which only provide information on the affinities of the compounds for the receptor.

It has now been found that the heterocyclic compounds of the invention have affinity for the quisqualate receptors and are antagonists in connection with this type of receptor which makes them useful in the treatment of any of the numerous indications caused by hyperactivity of excitatory amino acids and more specifically as neuroleptics.

Some compounds of the present invention have also shown glycine receptor activity.

The heterocyclic compounds of the invention have the general formula I

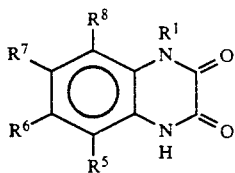

wherein $R^1$ is hydroxy, alkoxy, aryloxy, aralkyloxy, cycloalkylalkoxy, cycloalkoxy, or acyloxy;

$R^5$ and $R^6$ together form a further fused ring, which is substituted with hydrogen, halogen or CN, and $R^7$ and $R^8$ independently are hydrogen, $NO_2$, halogen, CN, $SO_2NR'R'$, $SO_2R'$, $CF_3$, or $OR'$, wherein $R'$ is hydrogen or $C_{1-4}$-alkyl; or $R^7$ and $R^8$ together form a further fused ring, which is substituted with hydrogen, halogen or CN, and $R^5$ and $R^6$ independently are hydrogen, $NO_2$, halogen, CN, $SO_2NR'R'$, $SO_2R'$, $CF_3$, or $OR'$, wherein $R'$ is hydrogen or $C_{1-4}$-alkyl.

The invention also relates to a method of preparing the abovementioned compounds. This method comprises a) reducing a compound having the formula II

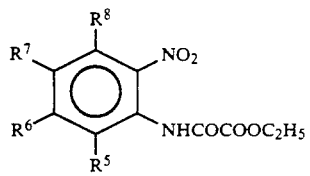

wherein $R^5$, $R^6$, $R^7$ and have the meanings set forth above, and optionally reacting the product thus formed with a compound having the formula III $$R^1-X \qquad III$$

wherein $R^1$ has the meaning set forth above, and X is a leaving group to form a compound of the formula I.

The pharmacological properties of the compounds of the present invention can be illustrated by determining their capability for displacing radioactively labelled 2-amino-3-hydroxy-5-methyl-4-isoxazolepropionic acid (AMPA) from the quisqualate type receptors. The antagonistic properties of the compounds is demonstrated by their capability to antagonize quisqualic acid stimulated $^3$H-GABA-efflux from cultured rat cortical neurones.

The displacement activity of the compounds may be shown by determining the $IC_{50}$ value which represents the concentration (μg/ml) which causes a displacement of 50% of the specific binding of $^3$H-AMPA.

The antagonism is measured by determining the $EC_{50}$ value which represents the concentration which reduces the rate of quisqualic acid stimulated $^3$H-GABA efflux by 50%.

$^3$H-AMPA binding

500 μl of thawed rat cerebral cortical membrane homogenate in Tris-HCl (30 mM), $CaCl_2$ (2.5 mM) and KSCN (100 mM) pH 7.1 were incubated at 0° C. for 30 min. with 25 μl $^3$H-AMPA (5 nM final concentration) and the test compound and buffer. Nonspecific binding was determined by incubation with L-glutamic acid (600 μM final concentration). The binding reaction was terminated by adding 5 ml of ice-cold buffer followed by filtration through Whatman GF/C glass fibre filters and 2×5 ml wash with ice-cold buffer. Bound radioactivity was measured by scintillation counting. $IC_{50}$ was determined by Hill analysis of at least four concentrations of test compound.

Cell cultures

Cerebral cortices of 16 day old mouse embryos are chopped in 0.4×0.4 mm cubes. The tissue is dissociated by mild trypsinization (0.1% (wt/vol) trypsin, 37° C., 15 min) and subsequently inoculated into poly-L-lysine-coated 3 cm Petri dishes containing a slightly modified DMEM (24.5 mM KCl, 30 mM glucose) supplemented with p-aminobenzoate (7μM), insulin (100 mU/1) and 10% (vol/vol) horse serum. Cells are maintained in culture for 5-7 days with the addition of the antimitotic agent cytosine arbinoside (40 μM) from day 2 in vitro to prevent glial proliferation. For further details and references see Drejer et al. Exp. Brain Res. 47, 259 (1982)).

Release experiments

Release experiments are performed using the model described by Drejer et al. (Life Sci. 38, 2077 (1986)). Cerebral cortex interneurons cultured in Petri dishes (30 mm) are added 100 μM gamma-vinyl-GABA one hour before the experiment in order to inhibit degradation of GABA in the neurons. 30 min. before the experiment 5 μCi $^3$H-GABA is added to each culture and after this preloading period the cell monolayer at the bottom of the dish is covered with a piece of nylon mesh to protect the cells against mechanical damage and to facilitate dispersion of medium over the cell layer. The preloading medium is removed and the Petri dishes are placed in a superfusion system. This system consists of a peristaltic pump continuously delivering thermostated 37° C. superfusion medium (HEPES buffered saline (HBS): 10 mM HEPES, 135 mM NaCl, 5 mM KCl, 0.6 mM M 1.0 mM $CaCl_2$ and 6 mM D-glucose; pH 7.4) from a reservoir to the top of the slightly tilted Petri dish. The medium is continuously collected from the lower part of the dish and delivered to a fraction collector. Initially, the cells are superfused with HBS for 15 min. (flow rate 2 ml/min.). The cells are stimulated for 30 sec. every 4 min. by changing the superfusion medium from HBS to a corresponding medium containing quisqualate and test compound. The release of $^3$H-GABA in the presence of quisqualate (stimulated release in cpm) are corrected for the mean basal release (Cpm) before and after the stimulation.

Test results obtained by testing some compounds employed in the present invention will appear from the following table 1.

TABLE 1

| Compound of example | $IC_{50}$ μg/ml | $K_i$ μg/ml |
| --- | --- | --- |
| 1b | 0.61 | 0.12 |
| 2c | 0.39 | 0.1 |
| 4b | 0.23 | 0.16 |
| 5b | 0.49 | 0.14 |

The pharmaceutical preparations or compositions comprising the compounds of the invention may be administered to humans or animals by oral or parenteral route.

An effective amount of the active compound or a pharmaceutically-acceptable salt thereof may be determined in accordance with the usual factors, such as the nature and severity of the condition and the weight of the mammal requiring treatment.

Conventional excipients are such pharmaceutically-acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose, and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or coloring substances and the like, which do not deleteriously react with the active compounds.

Injectable solutions or suspensions, preferably aqueous solutions with the active compound dissolved in polyhydroxylated castor oil are particularly suitable for parenteral administration.

Ampoules are convenient unit dosage forms.

Tablets, dragees, or capsules containing talc and/or a carrier or binder or the like are particularly suitable for oral administration. The carrier preferably is lactose and/or corn starch and/or potato starch.

A syrup, elixir, or the like can be used in the cases where a sweetened vehicle can be employed or is desired.

Generally, the compounds of this invention are dispensed in unit dosage form comprising 50-200 mg of active ingredient in or together with a pharmaceutically-acceptable carrier per unit dosage.

The dosage of the compounds according to this invention is 1-500 mg/day, e.g., about 100 mg per dose, when administered to patients, e.g., humans, as a drug.

A typical tablet which may be prepared by conventional tabletting techniques contains:

| Core: | |
|---|---|
| Active compound (as free compound or salt thereof) | 100 mg |
| Colloidal silicon dioxide (Aerosil ®) | 1.5 mg |
| Cellulose, microcryst. (Avicel ®) | 70 mg |
| Modified cellulose gum (Ac-Di-Sol ®) | 7.5 mg |
| Magnesium stearate | 1 mg |
| Coating | |
| HPMC approx. | 9 mg |
| *Mywacett ® 9-40 T approx. | 0.9 mg |

*Acylated monoglyceride used as plasticizer for film-coating

The free quinoxaline compounds of the present invention which form alkali metal or alkaline earth metal salts may be employed in such salt form. Such alkali metal or earth alkali metal salts are ordinarily formed by reacting the quinoxaline compound with an equivalent amount or excess of the selected alkali metal or earth alkali metal as the hydroxide, frequently and suitably by admixture in the presence of a neutral solvent, from which the salt may be precipitated or recovered in other conventional manner, e.g., by evaporation. Administration of a compound of the invention is often preferably in the form of a pharmaceutically-acceptable water-soluble alkali metal or earth alkali metal salt thereof, and orally, rectally, or parenterally in the form of a pharmaceutical composition wherein it is present together with a pharmaceutically-acceptable liquid or solid carrier or diluent.

The compounds of the invention, together with a conventional adjuvant, carrier, or diluent, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical composition and unit dosage forms thereof may comprise conventional ingredients in conventional proportions, with or without additional active compounds or principles, and such unit dosage forms may contain any suitable effective neuroleptic, especially quisqualate antagonistic, amount of the active ingredient commensurate with the intended daily dosage range to be employed. Tablets containing fifty (50) milligrams of active ingredient or, more broadly, ten (10) to two hundred (200) milligrams, per tablet, are accordingly suitable representative unit dosage forms.

Due to their high degree of neuroleptic, particularly quisqualate antagonistic, activity and their low toxicity, together presenting a most favorable therapeutic index, the compounds of the invention may be administered to a subject, e.g., a living animal body, in need of such neuroleptic treatment, elimination, alleviation, or amelioration of an indication which is sensitive to a change in the quisqualate receptor condition, often preferably in the form of an alkali metal or earth alkali metal salt thereof, concurrently, simultaneously, or together with a pharmaceutically-acceptable carrier or diluent, especially and preferably in the form of a pharmaceutical composition thereof, whether by oral, rectal, or parenteral (including subcutaneous) route, in an effective amount. Suitable dosage ranges are 50-200 milligrams daily, preferably 50-100 milligrams daily, and especially 70-100 milligrams daily, depending as usual upon the exact mode of administration, form in which administered, the indication toward which the administration is directed, the subject involved and the body weight of the subject involved, and the preference and experience of the physician or veterinarian in charge. Such method of treating may be described as the treatment of an indication caused by or related to hyperactivity of the excitatory neurotransmitters, and particularly the quisqualate receptors, in a subject in need thereof, which comprises the step of administering to the said subject a neurologically- or neuroleptically-effective amount of a quisqualate antagonistic quinoxaline compound of the invention.

The invention will now be described in further detail with reference to the following examples.

EXAMPLE 1 a. 4-Bromo-1-ethoxalylamino-2-nitronaphthalene

To a solution of 4.0 g (15.0 mmol) 4-bromo-2-nitro-1-naphthylamine and 4.0 ml (29.1 mmol) dry triethylamine in 200 ml dry tetrahydrofuran was added a solution of 3.8 ml (34.2 mmol) ethyl oxalylchloride in 30 ml dry tetrahydrofuran. The reaction mixture was stirred at 25° C. for 24 h, and then filtered and evaporated in vacuo. The residue was recrystallized (ethanol-water) to give 4.5 g (82%) of 4-bromo-1-ethoxalylamino-2-nitronaphthalene. M.p. 190°–1° C.

b. 4-Hydroxy-benzo[f]quinoxaline-2,3(1H,4H)-dione

A solution of 0.5 g (1.36 mmol) 4-bromo-1-ethoxalylamino-2-nitronaphthalene in 30 ml tetrahydrofuran was added 10 ml dimethylformamide and 0.7 ml 25% aqueous ammonia. The mixture was hydrogenated at atm. pressure by using 50 mg 5% Pd-C as a catalyst. The precipitated product was filtered off and washed with tetrahydrofuran. The filter cake was washed several times with 5% aqueous potassium hydroxide. Acidification of the filtrate with 4N hydrochloric acid and recrystallization (dimethylformamide-water) of the precipitated product gave 0.2 g (65%) 4-hydroxy-benzo[f]quinoxaline-2,3(1H,4H)-dione. M p. 270° C. decomp. $^1$H-NMR (DMSO-d$_6$): 12.1 (1H, broad s), 8.6 (1H, m), 7.7 (5H, m). MS (m/e): 228 (M+, 90%).

EXAMPLE 2 a. 4-Cyano-1-ethoxalylaminonaphthalene

To a solution of 6.73 g (40.0 mmol) 4-cyano-1-naphthylamine and 11.2 ml (80 mmol) dry triethylamine in 200 ml dry tetrahydrofuran was added at 0° C. a solution of 8.9 ml (80 mmol) ethyl oxalylchloride in 40 ml dry tetrahydrofuran. Stirring was continued at 25° C. for 1 h, and then the mixture was filtered and evaporated in vacuo. The residue was stirred with ethanol to give 10.0 g (94%) of 4-cyano-1-ethoxalylaminonaphthalene. M.p. 163.8° C.

b. 4-Cyano-1-ethoxalylamino-2-nitronaphthalene

A solution of 4.2 g (15.7 mmol) 4-cyano-1-ethoxalylaminonaphthalene in 125 ml glacial acetic acid was added 125 ml acetic anhydride. At 15° C. a solution of 12 ml 100% nitric acid in 60 ml glacial acetic acid was added dropwise. Stirring was continued at 25° C. for 24 h and then at 50° C. for 1.5 h. The reaction mixture was poured into 500 ml ice-water to give 3.5 g (72%). M.p. 178.0° C.

c. 6-Cyano-4-hydroxy-benzo[f]quinoxaline-2,3(1H,4H)-dione

A solution of 0.5 g (1.59 mmol) 4-cyano-1-ethoxalylamino-2-nitronaphthalene in 30 ml tetrahydrofuran was added 10 ml dimethylformamide and 0.7 ml 25% aqueous ammonia. The mixture was hydrogenated at atm. pressure by using 100 mg 5% Pd-C as a catalyst. The precipitated product was filtered off and washed with tetrahydrofuran. The filter cake was washed several times with 5% aqueous potassium hydroxide. Acidification of the filtrate with 4N hydrochloric acid gave 0.2 g (50%) of 6-cyano-4-hydroxy-benzo[f]quinoxaline-2,3(1H,4H)-dione. M.p. 275° C. decomp. IR (KBr): 3420 (m, broad) 330–2800 (m) 2220 (m) 1760 (s) 1585 (m) 1530 (m), 1370 (m) cm$^{-1}$.

EXAMPLE 3 a. 6-Bromo-2-ethoxalylamino-1-nitronaphthalene

To a solution of 1.0 g (3.75 ml) 6-bromo-1-nitro-2-naphthylamine and 0.8 ml (5.81 mmol) dry triethylamine in 100 ml dry tetrahydrofuran was added a solution of 0.7 ml (6.27 mmol) ethyl oxalylchloride in 25 ml dry tetrahydrofuran. The reaction mixture was stirred at 25° C. for 24 h, and then filtered and evaporated in vacuo. The residue was recrystallized (ethanol to give 1.2 g (87%) of 6-bromo-2-ethoxalylamino-1-nitronaphthalene. M.p. 175°–5° C.

b. 1-Hydroxy-benzo[f]quinoxaline-2,3(1H,4H)-dione

A solution of 0.5 g (1.36 mmol) 6-bromo-2-ethoxalylamino-1-nitronaphthalene in 30 ml tetrahydrofuran was added 10 ml dimethylformamide and 0.7 ml 25% aqueous ammonia. The mixture was hydrogenated at atm. pressure by using 100 mg 5% Pd-C as a catalyst. The precipitated product was filtered off and washed with tetrahydrofuran. The filter cake was washed several times with 5% aqueous potassium hydroxide. Acidification of the filtrate with 4N hydrochloric acid gave 0.15 g (50%) of 1-hydroxy-benzo[f]quinoxaline-2,3(1H,4H)-dione. M.p. 220° C. decomp. $^1$H-NMR (DMSO-d ): 12.3 (1H, broad s), 9.2 (1H, m), 7.5 (5H, m).

EXAMPLE 4 a. 5-Ethoxalylamino-6-nitroquinoline

To a solution of 1.3 g (6.9 mmol) 5-amino-6-nitroquinoline and 3.0 ml (21 mmol) dry triethylamine in 100 ml dry tetrahydrofuran was added a solution of 2.5 ml (22.3 mmol) ethyloxalylchloride. The reaction mixture was stirred at 80° C. for 1.5 h. After cooling to 25° C. the mixture was evaporated in vacuo and the residue was stirred with water to give 1.9 g (96%) of 5-ethoxalylamino-6-nitroquinoline. M.p. 180.7° C.

b. 4-Hydroxypyrido[3,2-f]quinoxaline-2,3(1H,4H)-dione 1.85 g (6.4 mmol) 5-ethoxalylamino-6-nitroquinoline in 100 ml tetrahydrofuran:dimethylformamide:25% aqueous ammonia (30:10:0.7) was hydrogenated at atm. pressure by using 200 mg 5% Pt-C as a catalyst. The precipitate was filtered off and washed with tetrahydrofuran. The filter cake was washed several times with 1N aqueous potassium hydroxide. Acidification of the filtrate with concentrated hydrochloric acid gave 0.78 g crude product. The crude product was recrystallized (dimethylformamide-water to give 0.58 g (34%) of 4-hydroxypyrido[3,2-f]quinoxaline-2,3(1H,4H)-dione, hydrochloride. M.p. decomp. 1H-NMR (DMSO-d6): 12.5 (1H, broad s), +, 100%), 184 (60%). 9.2–7.4 (5H, m). MS (m/e): 229 (M+, 100%), 184 (60%).

EXAMPLE 5 a. 5-Ethoxalylamino-1,2,3,4-tetrahydro-6-nitronaphthalene

A solution of ethyl oxalylchloride (1.3 ml, 11.6 mmol) in 10 ml of dry tetrahydrofuran was added dropwise to a solution of 5-amino-1,2,3,4-tetrahydro-6-nitronaphthalene (2.2 g, 11.4 mmol) and dry triethylamine (1.6 ml, 11.6 mmol) in 50 ml of dry tetrahydrofuran with stirring at 0° C. Then the mixture was stirred at room temperature for 30 min. An additional equivalent of dry triethylamine and ethyl oxalylchloride was added dropwise to the mixture. After 1 h at reflux temperature, the mixture was cooled on ice and filtered. The filtrate was evaporated to dryness, and the residue was recrystallized from ethanol affording 2.9 g (87%) of the pure title compound. M.p. 121°–122° C.; $^1$H-NMR (CDCl$_3$): 1.47 (t, J=Hz, 3H, CH$_3$), 1.66–2.02 (m, 4H, 2CH$_2$), 2.57–3.05 (m, 4H, 2CH$_2$), 4.47 (q, J=7 Hz, 2H, CH$_2$), 7.23 (d, J=9 Hz, 1H, ArH), 7.88 (d, J=9 Hz, 1H, ArH), 9.77 (broad s, 1H, NH).

b. 7,8,9,10-Tetrahydro-4-hydroxybenzo[f]quinoxaline-2,3(1H,4H)-dione

A solution of 25% ammonium hydroxide in water (0.7 ml) was added to a solution of 5-ethoxalylamino-1,2,3,4-tetrahydro-6-nitronaphthalene (0.30 g, 1 mmol) in a mixture of 10 ml of N,N-dimethylformamide and 30 ml of tetrahydrofuran. The mixture was hydrogenated at atmospheric pressure and room temperature in the presence of 5% platinum on carbon, until the starting material had disappeared. The mixture was filtered and the filtrate was discarded. Now the filter was washed with 5% aqueous potassium hydroxide, and the filtrate was acidified with 4N hydrochloric acid. The white precipitate was isolated by filtration and washed with water and ethanol to give 0.11 g (46%) of the title compound. M.p. >225° C. dec.; $^1$H-NMR (DMSO-$d_6$): 1.57–1.90 (m, 4H, 2CH$_2$), 2.50–2.93 (m, 4H, 2CH$_2$), 6.95 (d, J=9 Hz, 1H, ArH), 7.30 (d, J=9 Hz, 1H, ArH); appr. 11.1 (very broad s, 1H, NH); IR (KBr): 1670 cm$^{-1}$; MS (m/e): 232 (M$^+$, 87%).

EXAMPLE 6 a. 4-Bromo-1-ethoxalylamino-2-nitronaphthalene

A solution of ethyl oxalylchloride 1.1 ml, 9.8 mmol) in 15 ml of dry tetrahydrofuran was added dropwise to a solution of 1-amino-4-bromo-2-nitronaphthalene (0.9 g, 3.2 mmol) and dry triethylamine (1.37 ml, 9.8 mmol) in 20 ml of dry tetrahydrofuran with stirring at 0° C. The mixture was stirred for 1 h at room temperature, and filtered. The filtrate was evaporated to dryness, and the oily residue was boiled in 25 ml of 96% ethanol for 15 min. After cooling on ice, the solid product was isolated by filtration and washed with a small amount of cold ethanol to give 0.9 g (74%) of the title compound. M.p. 191°–192° C.; $^1$H-NMR (CDCl$_3$): 1.4 (t, J=7 Hz, 3H, CH$_3$), 4.40 (q, J=7 Hz, 2H, CH$_2$), 7.43–8.33 (m, 5H, ArH), 10.0 (broad s, 1H, NH).

b. 6-Bromo-4-hydroxybenzo[f]quinoxaline-2,3(1H,4H)-dione

A solution of 4-bromo-1-ethoxalylamino-2-nitronaphthalene (0.20 g, 0.5 mmol) in 20 ml of N,N-dimethylformamide was hydrogenated at room temperature and atmospheric pressure in the presence of a small amount of Raney-Ni. After the hydrogen uptake was complete, the mixture was filtered. The filtrate was evaporated to dryness and the residue was triturated with water and hot ethanol to give 100 mg (62%) of the title compound. M.p. >200° C. dec.; IR (KBr): 1690 cm$^{-1}$; MS (m/e): 306 (M$^+$, 2%), 308 ((M+2)$^+$, 2%).

EXAMPLE 7 a. 5-Bromo-8-ethoxalylaminoquinoline

To a solution of 2.5 g (17.4 mmol) 8-aminoquinoline in 60 ml dry tetrahydrofuran was added 2.8 ml (20.0 mmol) dry triethylamine and the reaction mixture was cooled to 0° C. 2.2 ml (19.7 mmol) ethyl oxalylchloride in 20 ml dry tetrahydrofuran was added dropwise and the reaction mixture was stirred at 25° C. for 1 h. The reaction mixture was evaporated in vacuo and the residue was stirred with water. The precipitate was filtered off (4.0 g).

The precipitate was dissolved in 100 ml dry dimethylformamide and 3.5 g (19.7 mmol) N-Bromosuccinimide was added. The reaction mixture was stirred at 25° C. for 18 h and at 100° C. for 1 h. The reaction mixture was evaporated in vacuo and the residue was stirred with water. The precipitate was filtered off to give 5.0 g (89%) of 5-Bromo-8-ethoxalylaminoquinoline. M.p. 152° C.

b. 5-Bromo-8-ethoxalylamino-7-nitroquinoline 100 ml 100% nitric acid was cooled to 0° C. and 1.0 g (3.1 mmol) 5-Bromo-8-ethoxalylaminoquinoline was added gradually. The reaction mixture was stirred at 25° C. for ½ h and then poured into 150 ml ice-water. The precipitate was filtered off, washed with water and ethanol to give 1.0 g (88%) of 5-Bromo-8-ethoxalylamino-7-nitroquinoline. M.p. 213°–215° C.

c. 6-Bromo-4-hydroxypyrido[2,3-f]quinoxaline-2,3-(1H,4H)-dione 0.5 g (1.4 mmol) 5-Bromo-8-ethoxalylamino-7-nitroquinoline in 30 ml ethanol was hydrogenated at atm. pressure by using 100 mg (5%) Pt/c as a catalyst. The reaction mixture was filtered and the filtrate was evaporated in vacuo. The residue was stirred with water and the precipitate was filtered off. The crude product was washed with ethanol to give 0.3 g (72%) of 6-Bromo-4-hydroxypyrido[2,3-f]quinoxaline-2,3(1H,4H)-dione. M.p. decomp. MS m/z: 307 (M 20%), 291 (70%), 156 (100%), 128 (70%).

d. 4-hydroxypyrido[2,3-f]quinoxaline-2,3(1H,4H)-dione 0.3 g (1.0 mmol) 6-Bromo-4-hydroxypyrido[2,3-f]quinoxaline-2,3(1H,4H)-dione in 20 ml dimethylformamide was hydrogenated at atm. pressure by using 300 mg Pd/c (5%) as a catalyst. The reaction mixture was filtered and the filtrate was evaporated in vacuo. The residue was stirred with ethanol and the precipitate was filtered off to give 0.2 g (90%) of 4-hydroxypyrido[2,3-f]quinoxaline-2,3(1H,4H)-dione. M.p. decomp. MS m/z: 229 (M$^+$, 25%), 212 (100%), 185 (45%).

EXAMPLE 8 a. 3-Ethoxalylamino-1,8-naphthalenedicarboxylic anhydride

To a solution of 3-amino-1,8-naphthalenedicarboxylic anhydride (2.13 g, 10 mmol) and dry triethylamine (1.53 ml, 11 mmol) in 90 ml of dry N,N-dimethylformamide, a solution of ethyl oxalyl chloride (1.23 ml, 11 mmol) in 10 ml of dry N,N-dimethylformamide was added dropwise at 50° C. under stirring. Stirring was continued for 30 min. at room temperature and then for 1.5 h at 0° C. The mixture was filtered and the precipitate was washed successively with water, ethanol and ether to afford 2.40 g (77%) of the pure title compound. M.p. 275°–276° C.; $^1$H-NMR (DMSO-$d_6$): 1.35 (t,J=7Hz, 3H, CH$_3$), 4.33 (q,J=7Hz, 2H, CH$_2$), 7.73 (t,J=8Hz, 1H, H-6), 8.20–8.83 (m, 4H, ArH), 11.33 (s,1H,NH).

b. 3-Ethoxalylamino-4-nitro-1,8-naphthalenedicarboxylic anhydride

Powdered potassium nitrate (0.51 g, 5 mmol) was added to a stirred solution of 3-ethoxalylamino-1,8-naphthalenedicarboxylic anhydride (1.57 g, 5 mmol) in 15 ml of conc. sulfuric acid at 0° C. Stirring was continued for 2 h at the same temperature, then the reaction mixture was poured into 150 ml of ice-water. The separated yellow solid was isolated by filtration and washed with water ethanol and ether. Trituration with a small amount of ethyl acetate afforded 1.38 g (77%) of the title compound. M.p. 221°-222° C.; 1H-NMR CDCl$_3$+DMSO-d$_6$): 1.43 (t,J=7Hz, $^3$H, CH$_3$), 4.37 (q,J=7Hz, 2H, CH$_2$), 7.70-8.60 (m, 3H, ArH), 8.82 (s, 1H, H-2), 11.3 (broad s, 1H, NH).

c.
11-Hydroxy-4H,6H-[2]benzopyrano[4,5-[f]quinoxaline-4,6,9,10(8H,11H)-tetrone A solution of 3-ethoxalylamino-1,8-naphthalenedicarboxylic anhydride (0.63 g, 1.75 mmol) in 50 ml of ethanol and 25 ml of N,N-dimethylformamide was hydrogenated at room temperature and atmospheric pressure over 5% platinum on carbon until the theoretical amount of hydrogen was taken up. The catalyst was removed by filtration and the filtrate was evaporated to dryness. The residue was triturated with ethanol to give the crude product, which was dissolved in 10 ml of 1N potassium hydroxide, treated with decolourizing charcoal, filtered and reprecipitated with 4M hydrochloric acid to give 100 mg (19%) of the title compound. M.p. 276° C. decomp. (DSC); IR (KBr): 1770, 1705, 1668 cm$^{-1}$; $^1$H-NMR (DMSO-d$_6$): 7.5-9.6 (m, 4H, ArH), 12.6 (broad s, 1H, NH or OH, only one exchangeable proton could be seen); MS m/e: 298 (M$^+$, 7%).

EXAMPLE 9 a. 1,2,3,4-Tetrahydro-8-nitro-5naphthalenesulfonamide

A solution of 1,2,3,4-tetrahydro-8-nitro-5-naphthylamine (4.4 g, 25 mmol) in a mixture of 90 ml of acetic acid and 100 ml of 4M hydrochloric acid was diazotised with a solution of sodium nitrite (1.74 g, 25 mmol) in 50 ml of water with stirring at 0° C. Stirring was continued for 1 h at this temperature. Meanwhile, a saturated solution of sulfur dioxide in 90 ml of acetic acid was prepared. Then a solution of cupric chloride (0.55 g, 4 mmol) in 20 ml of water was added, followed by the addition of the diazonium salt solution with stirring at 0° C., After 1 h at this temperature 50 mls of ice-water was added, and the solid product was isolated by filtration and washed with water to give 4.1 g of crude 1,2,3,4-tetrahydro-8-nitro-5-naphthalenesulfonyl chloride. Without further purification it was dissolved in 50 mls of dry tetrahydrofuran, and ammonia gas was bubbled through the solution for 30 min. with stirring at room temperature. The mixture was evaporated to dryness, and the solid residue was triturated with water, filtered off, and washed with water and ethanol to give 3.3 g (52%) of the title compound. M.p. 203°-206° C.; $^1$H-NMR (DMSO-d$_6$): 1.57-1.95 (m, 4H, 2CH$_2$), 2.62-3.33 (m, 4H, 2CH$_2$), 7.53 (s, 2H, NH$_2$), 7.65 (d,J=9Hz, 1H, ArH), 7.85 (d,J=9Hz, 1H, ArH).

b.
8-Amino-1,2,3,4-tetrahydro-5-naphthalenesulfonamide

A suspension of 1,2,3,4-tetrahydro-8-nitro-5-naphthalenesulfonamide (3.1 g, 12 mmol) in 150 ml of ethanol was hydrogenated at room temperature and atmospheric pressure over Raney-Ni. After the theoretical absorption, the reaction mixture was filtered and concentrated to dryness to give 2.6 g (95%) of the title compound. M.p. 216°-219° C. (ethanol); $^1$H-NMR (DMSO-d$_6$): 1.50-1.93 (m, 4H, 2CH$_2$), 2.17-2.57 (m, 2H, CH$_2$), 2.83-3.17 (m, 2H, CH$_2$), 5.29 (broad s, 2H, NH$_2$), 6.38 (d,J=9Hz, 1H, ArH), 6.75 (broad s, 1H, SO ), 7.35 (d,J=9Hz, 1H, ArH).

c.
5-Ethoxalylamino-8-ethoxalylaminosulfonyl-1,2,3,4-tetrahydrophthalene

Dry triethylamine (4.2 ml, 30 mmol) was added to a solution of 8-amino-1,2,3,4-tetrahydro-5-naphthalenesulfonamide (2.3 g, 10 mmol) in 100 ml of dry tetrahydrofuran. Then a solution of ethyl oxalyl chloride (3.4 ml, 30 mmol) in 30 ml of dry tetrahydrofuran was added dropwise at 0° C. with stirring. The mixture was stirred overnight at room temperature and filtered. The filtrate was evaporated to dryness and the residue was stirred with ethanol to give 2.5 g (59%) of the title compound. M.p. 160°-161° C.; $^1$H-NMR (DMSO): 1.23 (t,J=7Hz, $^3$H, CH$_3$), 1.30 (t,J=7Hz, 3H, CH$_3$), 1.55-1.92 (m, 4H, 2CH$_2$), 2.50-2.80 (m, 2H, CH$_2$), 2.92 (m, 2H, CH$_2$), 4.13 (q,J=7Hz, 2H, CH$_2$), 4.25 (q,J=7Hz, 2H, CH$_2$), 7.38 (d,J=9Hz, 1H, ArH), 7.77 (d,J=9Hz, 1H, ArH), 9.56 (very broad s, 1H, SO$_2$NH), 10.3 (s, 1H, NH).

d.
5-Ethoxalylamino-8-ethoxalylaminosulfonyl-1,2,3,4-tetrahydro-6-nitronaphthalene Potassium nitrate (0.24 g, 2.3 mmol) was added to a solution of 5-ethoxalylamino-8-ethoxalylaminosulfonyl-1,2,3,4-tetrahydronaphthalene (1.0 g, 2.3 mmol) in 12 ml of conc. sulfuric acid with stirring at 0° C. Stirring was continued for 2 h at this temperature, and then the mixture was poured into 75 ml of ice-water. The separated product was isolated by suction and washed repeatedly with water to give 0.64 g (58%) of sufficiently pure title compound. M.p. 140°-142° C. (ethanol); $^1$H-NMR (DMSO-d$_6$): 1.20 (t,J=7Hz, $^3$H, CH$_3$), 1.30 (t,J=7Hz, $^3$H, CH$_3$), 1.58-1.90 (m, 4H, 2CH$_2$), 2.60-2.90 (m, 2H, CH$_2$), 3.05-3.33 (m, 2H, CH$_2$), 3.95-4.60 (m, 4H, 2CH$_2$), 8.27 (s, 1H, ArH), 10.9 (broad s, 1H, NH, only one exchangeable proton could be seen).

e.
6-Ethoxalylaminosulfonyl-7,8,9,10-tetrahydro-4-hydroxybenzo[f]quinoxaline-2,3(1H,4H)-dione A suspension of 5-ethoxalylamino-8-ethoxalylaminosulfonyl-1,2,3,4-tetrahydro-6-nitronaphthalene (0.61 g, 1.3 mmol) in 100 ml of ethanol was hydrogenated at room temperature and atmospheric pressure in the presence of 60 mg of 5% platinum on carbon. After the theoretical absorption, the mixture was filtered and the filtrate was evaporated to dryness. The crude product (0.51g) was triturated with 50 ml of water, filtered off and then washed with water and a small amount of cold ethanol affording 0.28 g (53%) of the title compound. M.p. 267° C. decomp. (DSC); IR (KBr): 1725 cm$^{-1}$; $^1$H-NMR (DMSO-d$_6$): 1.23 (t,J=7Hz, $^3$H, CH$_3$), 1.57-1.93 (m, 4H, 2CH$_2$), 2.63-3.20 (m, 4H, 2CH$_2$), 4.20 (q,J=7Hz, 2H, CH$_2$), 7.98 (s, 1H, ArH), 11.5 (broad s, 1H, NH, only one exchangeable proton could be seen).

f)
7,8,9,10-Tetrahydro-4-hydroxy-6-sulfamoylbenzo[f]quinoxaline-2,3(1H,4H)-dione A suspension of 6-ethoxyalylaminosulfonyl-7,8,9,10-tetrahydro-4-hydroxybenzo[f]quinoxaline-2,3-(1H, 4H)-dione A suspension of 6-ethoxyalylaminosulfonyl-7,8,9,10-tetrahydro-4-hydroxybenzo[f]quinoxaline-2,3(1H,4H)-dione (0.20 g, 0.5 mmol) in 7 ml of conc. hydrochloric acid was heated to reflux with stirring for 1.5 h. The mixture was cooled to 0° C. and filtered. The isolated product was washed with water and dried to give 0.14 g (66%) of the title compound. M.p. 316° C. decomp. (DSC); IR (KBr): 1698 cm$^{-1}$; $^1$H-NMR (DMSO-d$_6$): 1.56–1.93 (m, 4H, 2CH$_2$), 2.60–3.27 (m, 4H, 2CH$_2$), 7.37 (broad s, 2H, SO$_2$NH$_2$), 7.92 (s, 1H, ArH), 11.3 (broad s, 1H, NH or OH), ca. 10.7–12.1 (very broad s, 1H, NH or OH), MS m/e: 311 (M$^+$, 18%).

EXAMPLE 10 a.
8-Acetyl-1,2,3,4-tetrahydro-5-methoxy-6-nitronaphthalene

A solution of 100% nitric acid (0.42 ml, 10 mmol) in 2 ml of acetic anhydride was added dropwise with stirring at −10° to −15° C. to a solution of 8-acetyl-1,2,3,4-tetrahydro-5-methoxynaphthalene (2.1 g, 10 mmol) in 25 ml of acetic anhydride containing one drop of conc. sulfuric acid. Stirring was continued for 20 min. at the same temperature, then the reaction mixture was poured into 100 ml of ice-water. The precipitated crystals were collected by filtration and washed with water and a small amount of cold ethanol to give 1.48 g (59%) of the title compound. M.p. 76°–77° C.; $^1$H-NMR (CDCl$_3$): 1.60–1.93 (m, 4H, 2CH$_2$), 2.57 (s, 3H, COCH$_3$), 2.67–3.13 (m, 4H, 2CH$_2$), 3.88 (s, 3H, OCH$_3$), 7.97 (s, 1H, H-7).

b. 8-Acetyl-1,2,3,4-tetrahydro-6-nitro-5-naphthylamine

A solution of 8-acetyl-1,2,3,4-tetrahydro-5-methoxy-6-nitronaphthalene (1.0 g, 4 mmol) in 15 ml of dry dimethylsulfoxide was heated to 100° C. and ammonia was passed into the solution for 3 h. After the solution was added to 100 ml of ice-water, the crude solid was filtered off and washed with water. Recrystallization from ethanol afforded 0.71 g (75%) of the pure title compound. M.p. 170°–172° C.; $^1$H-NMR (DMSO-d$_6$): 1.47–1.93 (m, 4H, 2CH$_2$), 2.27–2.63 (m, 2H, CH$_2$), 2.48 (s, $^3$H, COCH$_3$), 2.70–3.03 (m, 2H, CH$_2$), 7.50 (broad s, 2H, NH$_2$), 8.33 (s, 1H, H-7).

c.
8-Acetyl-5-ethoxalylamino-1,2,3,4-tetrahydro-6-nitronaphthalene

Dry triethylamine (0.7B ml. 5.6 mmol) was added to a solution of 8-acetyl-1,2,3,4-tetrahydro-6-nitro-5-naphthylamine (0.66 g, 2.B mmol) in 50 ml of dry tetrahydrofuran. Then a solution of ethyl oxalyl chloride (0.64 ml, 5.6 mmol in 5 ml of dry tetrahydrofuran was added dropwise with stirring at room temperature. Stirring was continued for 20 min. at the same temperature, then the mixture was heated to reflux for 3 h and cooled. The mixture was filtered, and the filtrate was evaporated to dryness. The oily residue was treated with 25 ml of water overnight, and the precipitated solid was isolated by filtration and washed successively with water, cold ethanol and light petroleum to give 0.78 g (83%) of the pure title compound. M.p. 120°–121° C.; $^1$H-NMR CDCl$_3$): 1.42 (t,J=7Hz, 3H, CH$_2$CH$_3$), 1.60–1.93 (m, 4H, 2CH$_2$), 2.50–3.17 (m, 4H, 2CH$_2$), 2.58 (s, 3H, COCH$_3$), 4.37 (q,J=7Hz, 2H, CH$_2$CH$_3$), 8.00 (s, 1H, H-7), 9.57 (broad s, 1H, NH).

d.
6-Acetyl-7,8,9,10-tetrahydro-4-hydroxybenzo[f]quinoxaline-2,3(1H,4H)-dione

A solution of 8-acetyl-5-ethoxalylamino-1,2,3,4-tetrahydro-6-nitronaphthalene (0.67 g, 2 mmol) in 100 ml of ethanol was hydrogenated at room temperature and atmospheric pressure over 50 mg of 5% platinum on carbon for 1 h. Then 50 ml of N,N-dimethylformamide was added to dissolve the precipitated solid, and the catalyst was removed by filtration. The filtrate was concentrated and the residue was washed with 50 ml of ethanol to give 0.40 g (73%) of the title compound. M.p. >200° C. decomp. (DSC); IR (KBr): 1709, 1677 cm$^{-1}$, $^1$H-NMR (DMSO-d$_6$): 1.43–1.93 (m, 4H, 2CH$_2$), 2.57 (s, $^3$H, COCH$_3$), 2.53–3.07 (m, 4H, 2CH$_2$), 7.57 (s, 1H, H-7), 11.4 (very broad s, 2H, OH and NH); MS (m/e: 274 (M$^+$, 100%).

In conclusion, from the foregoing, it is apparent that the present invention provides novel neurologically-effective quisqualate antagonist quinoxaline compounds and salts thereof, having advantageous and unpredictable properties, as well as novel pharmaceutical compositions thereof and method of treating therewith, all possessed of the foregoing more specifically-enumerated characteristics and advantages.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope of the appended claims.

We claim:
1. A quinoxaline compound having the formula

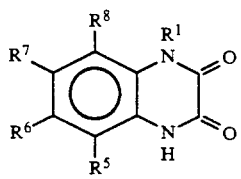

I wherein
R$^1$ is hydroxy; and
R$^5$ and R$^6$ together form a fused phenyl or cyclohexyl ring which is optionally substituted with halogen or CN; and R$^7$ and R$^8$ independently are hydrogen, hydroxy, NO$_2$, halogen, CN, CF$_3$, C$_{1-4}$-alkoxy, SO$_2$NR'R', or SO$_2$R', wherein R' is hydrogen or C$_{1-4}$-alkyl; or
R$^5$ and R$^6$ independently are hydroxy, hydrogen, NO$_2$, halogen, CN, CF$_3$, C$_{1-4}$-alkoxy, SO$_2$NR'R' or SO$_2$R', wherein R' is hydrogen or C$_{1-4}$-alkyl; and R$^7$ and R$^8$ together form a fused phenyl ring which is optionally substituted with halogen or CN.

2. A pharmaceutical composition useful as a neuroleptic comprising an effective amount of a compound having the formula I

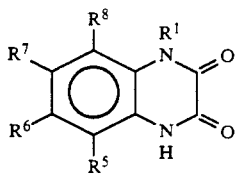

wherein

R[1] is hydroxy; and

R[5] and R[6] together form a fused phenyl or cyclohexyl ring which is optionally substituted with halogen or CN; and R[7] and R[8] independently are hydrogen, hydroxy, $NO_2$, halogen, CN, $CF_3$, $C_{1-4}$-alkoxy, $SO_2NR'R'$, or $SO_2R'$, wherein R' is hydrogen or $C_{1-4}$-alkyl; or R[5] and R[6] independently are hydroxy, hydrogen, $NO_2$, halogen, CN, $CF_3$, $C_{1-4}$-alkoxy, $SO_2NR'R'$ or $SO_2R'$, wherein R' is hydrogen or $C_{1-4}$-alkyl; and R[7] and R[8] together form a fused phenyl ring which is optionally substituted with halogen or CN.

3. A method of treating an indication due to hyperactivity of the excitatory neurotransmitters, in a subject in need thereof, which comprises the step of administering to the said subject an effective amount of a compound having the formula I

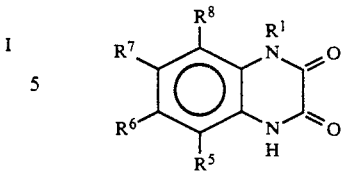

wherein

R[1] is hydroxy; and

R[5] and R[6] together form a fused phenyl or cyclohexyl ring which is optionally substituted with halogen or CN; and R[7] and R[8] independently are hydrogen, hydroxy, $NO_2$, halogen, CN, $CF_3$, $C_{1-4}$-alkoxy, $SO_2NR'R'$, or $SO_2R'$, wherein R' is hydrogen or $C_{1-4}$-alkyl; or R[5] and R[6] independently are hydroxy, hydrogen, $NO_2$, halogen, CN, $CF_3$, $C_{1-4}$-alkoxy, $SO_2NR'R'$ or $SO_2R'$, wherein R' is hydrogen or $C_{1-4}$-alkyl; and R[7] and R[8] together form a fused phenyl ring which is optionally substituted with halogen or CN.

4. The compound 4-hydroxy-benzo[f]quinoxaline-2,3-(1H,4H)-dione.

5. The compound 6-cyano-4-hydroxybenzo [f]quinoxaline-2,3(1H,4H)-dione.

6. The compound 7,8,9,10-tetrahydro-4-hydroxybenzo[f]quinoxaline-2,3(1H,4H)-dione.

7. The pharmaceutical composition according to claim 2 in the form of an oral dosage unit containing about 50–200 mg of the active compound.

8. The method according to claim 3 wherein said compound is administered in the form of an oral dosage unit containing about 50–200 mg of the active compound.

9. The method according to claim 3 wherein said compound is administered in the form of a pharmaceutical composition together with a pharmaceutically acceptable carrier or diluent.

* * * * *